United States Patent [19]

Davis et al.

[11] Patent Number: 5,336,191
[45] Date of Patent: Aug. 9, 1994

[54] SURGICAL NEEDLE ASSEMBLY

[75] Inventors: Richard E. Davis, Grand Rapids; William J. Greenhoe, Rockford, both of Mich.

[73] Assignee: DLP, Incorporated, Grand Rapids, Mich.

[21] Appl. No.: 930,098

[22] Filed: Aug. 13, 1992

[51] Int. Cl.$^5$ .................... A61M 5/158; A61M 5/32
[52] U.S. Cl. .................... 604/165; 604/274
[58] Field of Search .................... 604/164, 165, 274; 128/754

[56] References Cited

U.S. PATENT DOCUMENTS

| | | | |
|---|---|---|---|
| 2,426,535 | 8/1947 | Turkel | 128/754 |
| 3,175,554 | 3/1965 | Stewart . | |
| 3,515,137 | 6/1970 | Santomieri | 604/165 |
| 3,628,524 | 12/1971 | Jamshidi . | |
| 3,630,192 | 12/1971 | Jamshidi . | |
| 4,256,119 | 3/1981 | Gauthier . | |
| 4,266,555 | 5/1981 | Jamshidi . | |
| 4,340,066 | 7/1982 | Shah | 128/754 |
| 4,396,021 | 8/1983 | Baumgartner . | |
| 4,403,617 | 9/1983 | Tretinyak | 128/754 |
| 4,445,893 | 5/1984 | Bodicky | 604/165 |
| 4,609,370 | 9/1986 | Morrison . | |
| 4,655,226 | 4/1987 | Lee . | |
| 4,667,684 | 5/1987 | Leigh . | |
| 4,758,218 | 7/1988 | Kiefer et al. . | |
| 4,799,495 | 1/1989 | Hawkins et al. | 128/754 |
| 4,838,282 | 6/1989 | Strasser et al. | 128/754 |
| 4,844,087 | 7/1989 | Garg | 128/754 |
| 4,846,804 | 7/1989 | Davis et al. . | |
| 4,881,551 | 11/1989 | Taylor . | |
| 4,967,762 | 11/1990 | De Vries . | |
| 5,005,585 | 4/1991 | Mazza . | |
| 5,026,355 | 6/1991 | Sweeney et al. . | |
| 5,031,634 | 7/1991 | Simon . | |

OTHER PUBLICATIONS

Medi–tech, Incorporated, Crown Biopsy Needle, Apr. 1985.
Medi–tech, Incorporated, Chiba "Skinny" Needle, May 1985.

*Primary Examiner*—Paul J. Hirsch
*Attorney, Agent, or Firm*—Varnum, Riddering, Schmidt & Howlett

[57] ABSTRACT

A surgical needle with a stylet selectively received within the lumen of a cannula is shown where establishing and maintaining a desired angular orientation between the stylet and cannula is achieved. The orientation may be determined in one of several ways. Preferably, a projection is mounted to the cannula hub which is selectively received in a recess of the stylet cap when the stylet and cannula are in the desired orientation. Alternatively, a pair of flexible arms may be mounted to the stylet cap wherein detents on the distal ends of the flexible arms are selectively received within complementary depressions on the cannula hub when the stylet and cannula are in the desired orientation. Also, a longitudinal rib on the stylet cap and a projection on the cannula hub can be visually inspected or can be felt by the user to determine the orientation. Finally, a projection from the cannula hub may be selectively received within a slot on the stylet cap to ensure proper alignment of the stylet and cannula.

12 Claims, 5 Drawing Sheets

SURGICAL NEEDLE ASSEMBLY

BACKGROUND OF THE INVENTION

1. Field Of the Invention

This invention relates to a surgical needle assembly for performing hand-held surgical medical procedures such as obtaining subcutaneous tissue cell samples and, more particularly, to an improved cannula hub and cooperating stylet cap for quickly and surely determining the orientation of the stylet with respect to the cannula before commencement of the procedure.

2. Description of Related Art

Several medical procedures have been developed which make use of a hand-held surgical needle assembly comprising, among other elements, a cannula and a styler. Such procedures include biopsy, angiography, and spinal and epidural procedures. The biopsy procedure is used to obtain subcutaneous biopsy tissue samples and cell samples for detailed analysis. Biopsy procedures range from surgical examination of the internal tissue and large-bore core biopsies, to a less intrusive procedure commonly known as fine-needle aspiration. In this procedure, a fine or thin biopsy needle, sometimes called a "skinny needle", is introduced by penetration into the patient's body, and its tip is brought into contact with the tissue to be sampled. Suction or negative pressure is applied to the outboard end of the needle thereby drawing fluid and cells of the tissue to be sampled into the needle for removal from the patient. Because the needles used in aspiration biopsy procedures are fine or narrow, this procedure is minimally intrusive and can most often be performed in the physician's office as outpatient surgery. Fine-needle aspiration biopsies have replaced a large number of the more intrusive surgical biopsies previously performed.

The needle used for the aspiration procedure typically comprises a cannula formed with a contoured distal end and a stylet formed with a matching contour at its distal end. The stylet is received snugly but freely slidably within the lumen of the cannula to provide rigidity and a solid end for the needle, as opposed to a hollow tip, for introduction of the needle into the patient's body. After the tip or distal end of the needle reaches the tissue to be sampled, the stylet is removed, whereupon negative pressure may be applied to the hub of the cannula.

A wide variety of contour shapes for the distal ends of the cannula and stylet have been developed and may be employed in conjunction with the invention. In most cases, it is imperative that the stylet have a certain angular or rotational orientation with respect to the cannula as the needle is introduced into the patient's body to minimize trauma. Several different means have previously been incorporated in a handle or hub of the cannula and a cap of the stylet to indicate and maintain proper angular orientation of the stylet with respect to the cannula. The cannula hub typically comprises a solid member for mounting the cannula which the physician may grasp when using the needle. The cannula hub has an aperture for telescopically receiving the stylet. The stylet cap traditionally comprises a hollow cap which is telescopically received on the cannula hub. The cap also supports the stylet.

An example of a cooperating stylet cap and cannula hub is disclosed in U.S. Pat. No. 3,175,554, issued Mar. 30, 1965, to R. A. Stewart. Stewart illustrates a radially extending lug on the stylet cap which cooperates with a notch on the cannula hub to obtain the desired orientation of the stylet with respect to the cannula. U.S. Pat. No. 4,655,226, issued Apr. 7, 1987, to P. F. Lee, discloses a longitudinally extending lug on the stylet cap which interacts with a notch on the cannula handle to maintain proper angular orientation. A similar device is disclosed in U.S. Pat. No. 4,846,804, issued Jul. 11, 1989 to R. E. Davis et al. U.S. Pat. No. 4,266,555, issued May 12, 1981 to K. Jamshidi discloses a flat surface on a cylindrical stylet cap and cylindrical bore of a cannula hub to maintain the angular orientation. A lug and L-shaped channel are employed on the stylet cap and cannula hub in U.S. Pat. No. 3,630,192, issued Dec. 28, 1971 to K. Jamshidi, U.S. Pat. No. 4,609,370, issued Sep. 2, 1986 to P. C. Morrison, and U.S. Pat. No. 3,628,524, issued Dec. 21, 1971 to K. Jamshidi.

These prior references disclose various needle constructions in which mechanical interlocking means are provided to establish the angular orientation between the stylet and cannula of a needle. None of the needles disclosed in the prior art identified hereinabove includes simple visual means for checking the angular orientation of the stylet with the respect to the cannula. In addition, the prior devices as disclosed fail to show simple means to verify the angular orientation of the stylet and the cannula by touch.

SUMMARY OF INVENTION

The surgical needle according to the invention, on the other hand, provides simple visual means, mechanical interlocking means, and means which the user may touch to determine the angular orientation of the stylet with respect to the cannula. The surgical needle according to the invention is suitable for use in a wide variety of medical procedures such as biopsy, angiography, and spinal and epidural applications.

More particularly, the invention comprises an improved surgical needle including a cannula member and a stylet member, the cannula member comprising a cannula handle or hub and a cannula having a proximal end mounted to the cannula handle. A distal end of the cannula is opposite from the cannula handle. The stylet member comprises a stylet handle or cap and a stylet having a proximal end affixed to the stylet handle. A distal end of the stylet is opposite from the stylet handle. The stylet is removably receivable within the lumen of the cannula. The axial dimensions of the stylet and the cannula are so related that when the stylet is fully received within the cannula with the stylet and cannula handles adjacent to each other, the distal ends are coterminous.

The distal ends of the stylet and cannula are contoured to cooperate in forming a predetermined needle tip configuration when the stylet is fully received in the lumen of the cannula in a predetermined angular relation therewith. The respective handles include indicators for determining the angular relation of the cannula and the stylet. In one embodiment, one of the handles includes a receivable projection formed on an exterior surface. The other of the handles comprises a hollow body having a locking recess formed on an interior surface thereof. The other handle receives at least a portion of the one handle within the hollow body when the stylet is fully received in the cannula. The receivable projection and locking recess are so formed and situated that the receivable projection is snap-locked in the locking recess when the cannula and stylet are in the predetermined angular relation.

In a further embodiment of the needle according to the invention, the indicators comprise a detent extending from one of the handles in a direction to overlie the other of the handles when the stylet is fully received in the lumen of the cannula and a depression is provided on the other handle in a position aligned with the detent when the stylet and cannula are in the predetermined angular relation. Preferably, a pair of detents are carried on a pair of flexible arms extending from the respective handle. The arms are manually depressible to cause the detents to be received in a pair of depressions of the other handle, but only when the stylet and the cannula are in the predetermined angular relation. Alternatively, only a single detent, arm and depression can be incorporated.

In another embodiment of the invention the indicators comprise at least one guide projection mounted on one of the handles. A longitudinal rib is mounted on the other of the handles. The guide projection and longitudinal rib are aligned when the stylet and cannula are in the predetermined angular relation.

In another embodiment of the invention the indicators comprise a slot formed in one of the handles. A guide projection is selectively received in the slot when the stylet and cannula are in the predetermined angular relation.

In another embodiment of the invention, the indicators comprise a receivable projection mounted on one of the handles and a recess mounted on the other of the handles. The projection is received within the recess when the stylet and cannula are in the predetermined angular relation.

Preferably, the contoured distal end of the cannula is angled at an acute angle with respect to the longitudinal axis of the cannula. The contoured distal end of the stylet is angled such that it lies on the same plane as the contoured end of the cannula when the stylet is fully received in the lumen of the cannula in the predetermined angular relation.

BRIEF DESCRIPTION OF THE DRAWINGS

The invention will now be described with reference to the drawings wherein.

DESCRIPTION OF THE ILLUSTRATED EMBODIMENT

Figure 1:
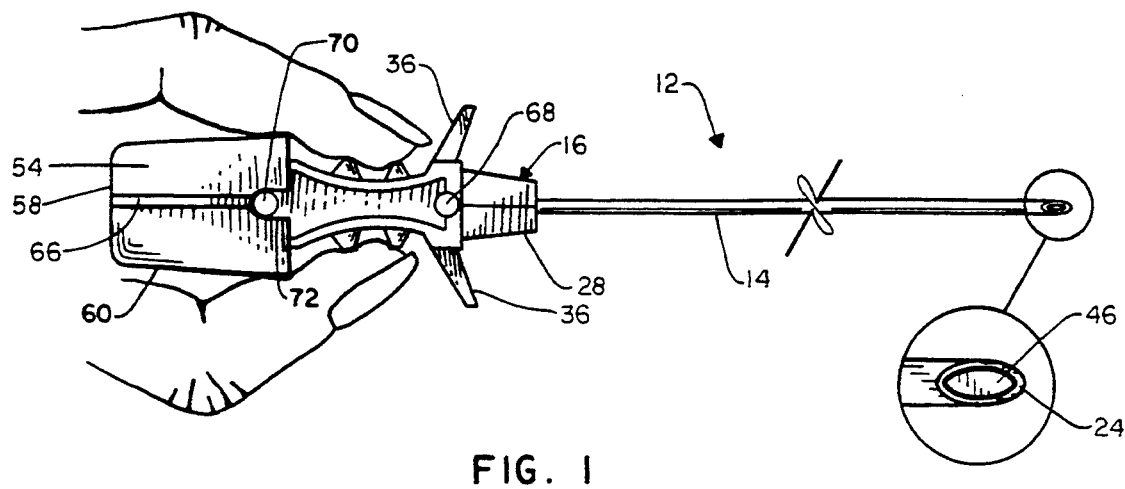
FIG. 1 is a top plan view of the stylet cap and cannula hub interconnected.

Referring now to the drawings and to FIGS. 1–4 in particular, a surgical needle 12 comprises a cannula 14 mounted to a cannula handle or hub 16 and a styler 18 mounted in a stylet handle or cap 20. The cannula 14 has a lumen 22 extending the length thereof and a distal end 24 which is preferably machined to an acute angle relative to the longitudinal axis of the cannula 14. A proximal end 26 of the cannula 14 is fixedly mounted in a cannula mounting 28 on one end of the cannula hub 16.

The cannula hub 16 comprises a body portion 34, a pair of flanges 36 on opposite sides of the hub 16, a pair of guide flanges 38 also on opposite sides of the hub 16 and a syringe mounting 40 on the end of the hub 16, opposite the cannula mounting 28. A reservoir 42 extends through the length of the cannula hub, i.e. from the syringe mounting 40 to the cannula mounting 28. The reservoir 42 is in fluid communication with the lumen 22. The reservoir 42 and lumen 22 create an aperture which extends the entire length of the cannula hub 16 and cannula 14.

Figure 5:
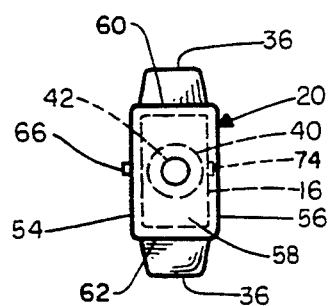
FIG. 5 is an end elevational view of the stylet cap and cannula hub.

The stylet 18 has a distal end 46 which is machined to an angle with respect to the longitudinal axis of the stylet 18. A proximal end 48 of the stylet 18 is fixedly mounted in a stylet mounting 50 of the stylet cap 20. The stylet cap 20 comprises a body portion 52, a top 54 (FIG. 5), a bottom 56 (FIG. 5) and an end wall 58.

The end of the stylet cap 20 which is opposite the end wall 58 is open and the body portion 52 of the stylet cap 20 is hollow, whereby a portion of the cannula hub 16 may be selectively received within the stylet cap 20. The guide flanges 38 of the cannula hub 16 engage the interior surface of the hollow stylet cap 20 to guide the cannula hub 16 into and out of the stylet cap 20.

The surgical needle 12, according to the invention, may be used for a fine-needle aspiration biopsy to obtain a sample of certain tissue cells and the surrounding fluid. The distal ends of the cannula 24 and stylet 46 are inserted into the patient's body. The stylet is concentrically mounted within the cannula 14 to provide support for the cannula 14 as the needle 12 penetrates the body and to prevent material from entering the lumen 22. When the tip of the cannula reaches the tissue to be sampled, the stylet 18 is removed from the cannula 14. A syringe (not shown) or other suitable device is attached to the syringe mounting 40 to create negative pressure within the reservoir 42 and the lumen 22. This negative pressure causes a small amount of the fluid around the distal end 24 of the cannula and cells of the tissue being sampled to be drawn into the lumen 22 and reservoir 42. Thereafter, the cannula 14 is removed from the patient and the tissue cells and fluid within the lumen 22 and reservoir 42 are expelled from the needle 12 for testing.

Preferably, the distal ends of the cannula 14 and stylet 18 are contoured to permit easy penetration of the needle 12 into the patient's body. In the preferred embodiment, the distal end 24 of the cannula 14 is angled with respect to the longitudinal axis of the cannula. The distal end 46 of the stylet 18 is similarly angled such that the distal end 46 of the stylet 18 lies along the same plane as the distal end 24 of the cannula when the stylet 18 is correctly mounted within the cannula 14.

As the angled tip of the preferred embodiment of the needle 12 penetrates the patient's body, it is imperative that the distal end 46 of the stylet 18 lie on the same plane as the distal end 24 of the cannula 14. Proper orientation will minimize trauma to the tissue and organs into which the needle is inserted. The needle 12 according to the invention comprises various indicators for quickly and surely determining the angular orientation of the stylet 18 with respect to the cannula 14.

The first embodiment of the needle incorporates visual and mechanical indicators for determining the angular relation of the cannula 14 and the stylet 18. The first visual indicator comprises a longitudinal rib 66 mounted on the top 54 of the stylet cap 20. The rib 66 extends along the longitudinal axis of the stylet 18. A first projection 68 is mounted on one side of the cannula hub 16. When the stylet 18 is properly aligned with the cannula 14, then the longitudinal rib 66 and the first projection 68 are both on the same side of the needle 12 and are aligned along the longitudinal axis of the needle 12, as seen in FIG. 1.

In use, the user may visually observe the longitudinal rib 66 and the first projection 68 to ensure proper alignment of the stylet 18 and the cannula 14. Alternatively, the user may evaluate the orientation of the stylet 18 by placing his or her thumb or finger on the top 54 of the cap. If the user feels the longitudinal rib 66 and the first projection 68 on the same side of the needle 12, then he or she may be confident that the stylet 18 is in proper alignment with the cannula 14.

Figure 2:
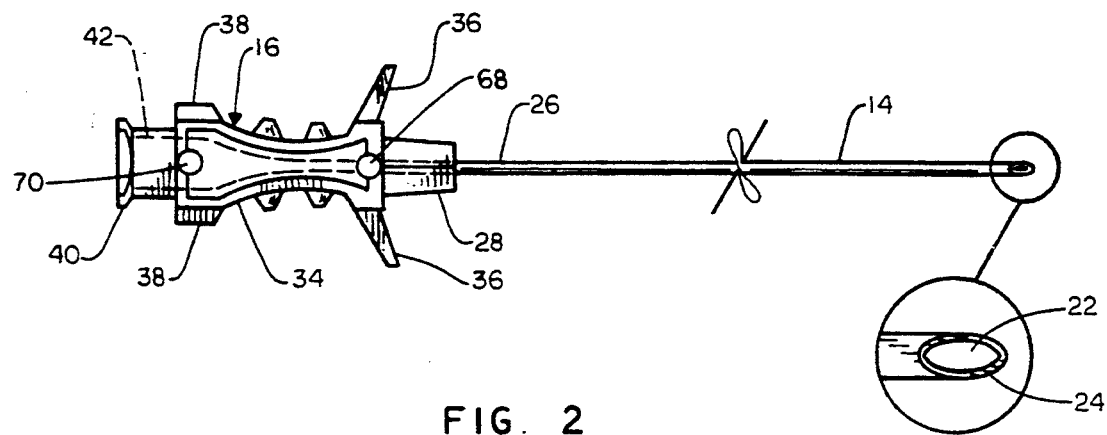
FIG. 2 is a top plan view of the cannula hub and cannula.
Figure 3:
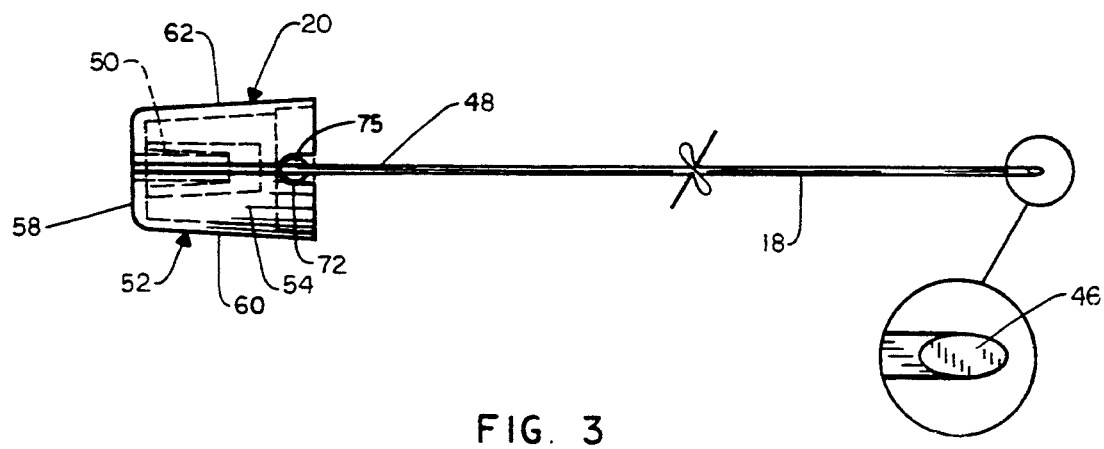
FIG. 3 is a top plan view of the stylet cap and stylet.
Figure 4:
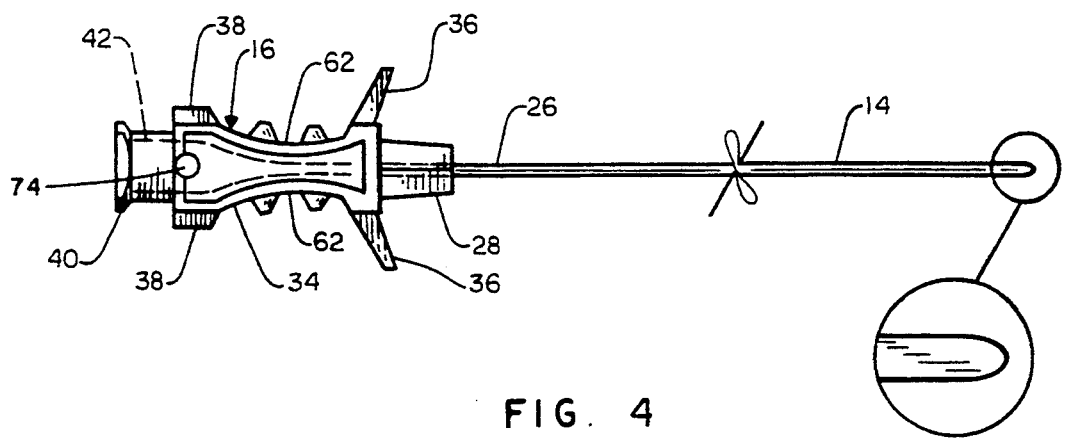
FIG. 4 is a bottom plan view of the cannula hub and cannula.

The first embodiment of the needle 12 according to the invention also includes an additional indicator for determining the angular relation of the stylet 18 and the cannula 14 which comprises a first interlocking guide means on the stylet cap 20 and cannula hub 16. The first interlocking guide means comprises a second projection 70 on one side of the cannula hub 16 and a slot 72 on the top 54 of the stylet cap 20. As seen in FIG. 2, the second projection 70 is mounted adjacent to the guide flanges 38 and the syringe mounting 40. As seen in FIG. 3, the slot 72 is located opposite the end wall 58 and is in alignment with the longitudinal rib 66. The second projection 70 is selectively received within the slot 72 of the stylet cap 20 when the stylet 18 is properly inserted within the cannula 14, as seen in FIG. 1.

Figure 6:
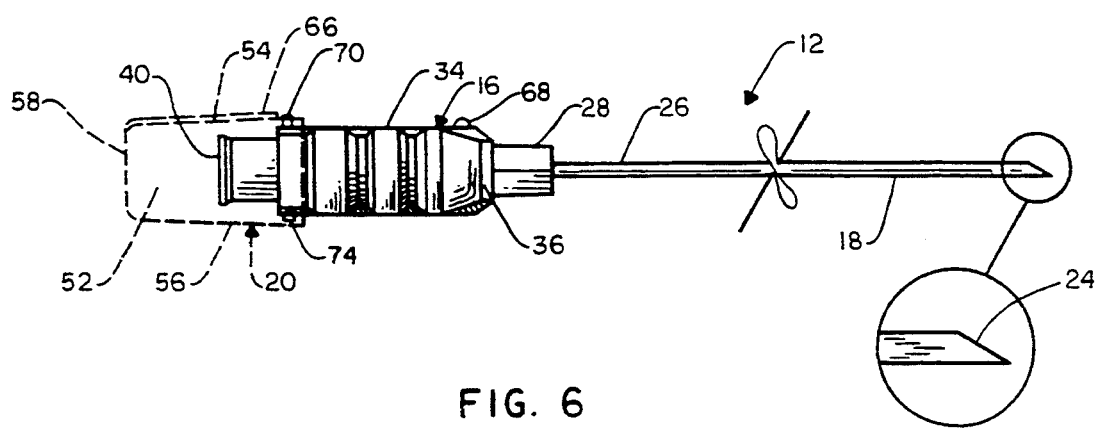
FIG. 6 is a side elevational view of the stylet cap and cannula hub with the stylet cap shown in phantom lines.

The first embodiment of the needle 12 according to the invention also includes a second interlocking guide means on the stylet cap 20 and the cannula hub 16. The second interlocking guide means comprises a third projection 74 on the cannula hub 16 and a recess 75 formed on the inside surface of the bottom of the stylet cap 56 of the stylet cap 20. The third projection 74 is selectively received within the recess 75 when the stylet 18 is inserted within the cannula 14 in the desired angular orientation, as seen in FIGS. 1 and 6. The third projection 74 extends outwardly from the cannula hub 16 a limited distance such that the thickness of the cannula hub 16 and third projection 74 is slightly more than the opening of the stylet cap 20. However, the third projection can be received in the stylet cap along with the syringe mounting 40, guide flanges 38 and body 34 of the cannula hub 16 upon minor deformation of the stylet cap by squeezing the sides 60 and 62 of the cap 20. The third projection is preferably complementary in shape to the recess 75 such that when the stylet cap is properly mounted on the cannula hub, the third projection 74 will effectively "snap" into the recess 75.

The stylet cap 20 can be removed from the cannula hub 16 by applying a squeezing force to the first and second side walls, 60 and 62, sufficient to deform the stylet cap slightly until the third projection 74 is removed from the recess 75 and the stylet cap 20 and stylet 18 can be slidably removed from the cannula hub 16 and cannula 14.

As seen in FIG. 1, when the stylet 18 is properly mounted in the cannula 14 the cannula hub 16 is slidably received within the stylet cap 20 and the third projection 74 is received within the recess 75, effectively "locking" the stylet cap 20 to the cannula hub 16. The user may evaluate the angular relation of the cannula 14 and the stylet 18 by attempting to slidably remove the stylet from the cannula. If properly mounted, the stylet cap 20 will not be easily removed from the cannula hub 16 because the third projection 74 is received within the recess 75.

Secondly, the alignment may be evaluated if the user examines the alignment of the longitudinal rib 66 and the first projection 68. These two indicators should be on the same side of the needle 12 and should be in alignment along the longitudinal axis of the needle 12. Finally, the user may evaluate the alignment of the cannula 14 and stylet 18 by examining the second projection 70 and slot 72. If properly aligned, the second projection 70 should be received within the slot 72.

Figure 7:
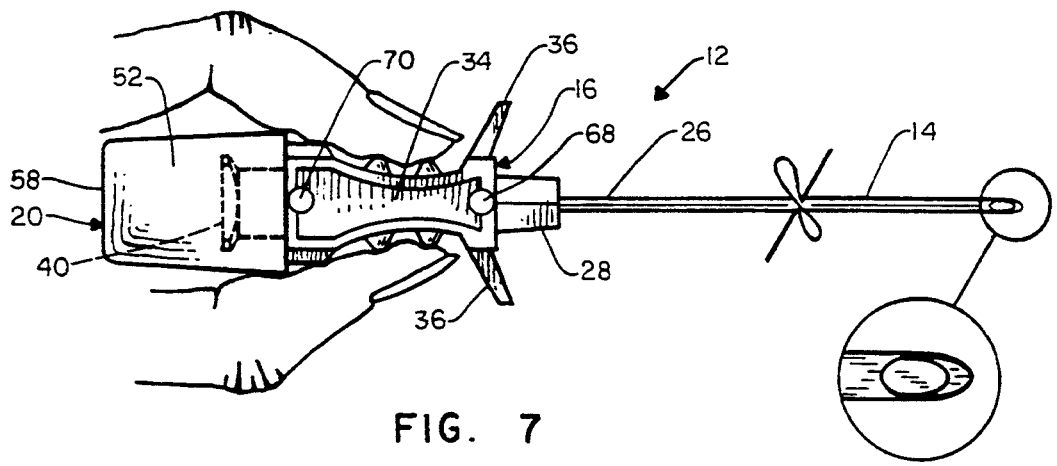
FIG. 7 is a top plan view of the stylet cap mounted incorrectly on the cannula hub.
Figure 8:
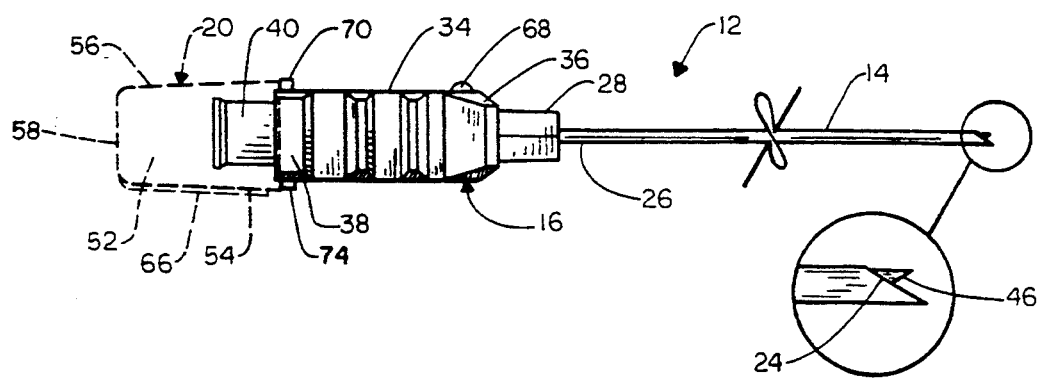
FIG. 8 is a side elevational view of the stylet cap shown in phantom lines mounted incorrectly on the cannula hub as seen in FIG. 7.

If the styler 18 were inserted into the cannula 14 incorrectly as seen in FIGS. 7 and 8, the angled distal end 46 of the stylet 18 would be 180° out of alignment with the angled distal end 24 of the cannula 14, as seen in FIG. 8. The user of the needle 12 would be able to immediately detect the misalignment of the stylet 18 within the cannula 14 because the third projection 74 would not be received in the recess 75, effectively locking the stylet cap 20 and cannula hub 16. Secondly, the longitudinal rib 66 of the stylet cap 20 would not be in alignment with the first projection 68 of the cannula hub 16. Finally, the second projection 70 is not received within the slot 72 of the stylet cap 20. Rather, the second projection 70 abuts the edge of the bottom 56 of the stylet cap 20.

Although the distal ends of the stylet 18 and cannula 14 disclosed above are an angle or a wedge, it is understood that any contoured end in which the alignment between the stylet 18 and cannula 14 is maintained may be utilized with the invention.

Figure 9:
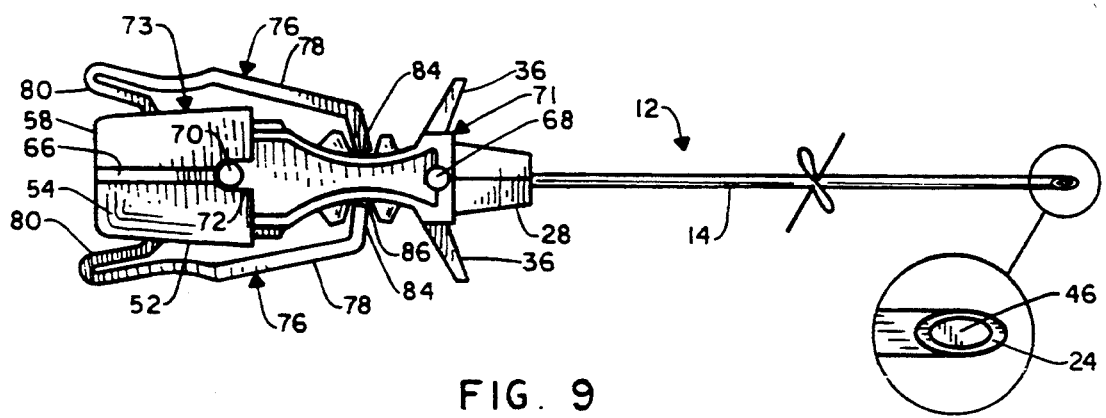
FIG. 9 is a top plan view of a second embodiment of the stylet cap and cannula hub interconnected.
Figure 10:
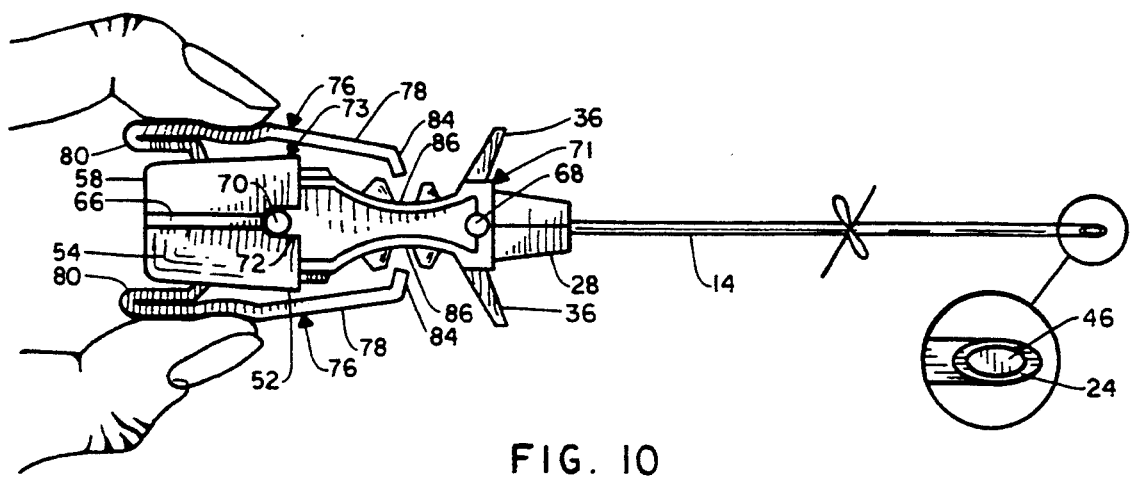
FIG. 10 is a top plan view of the stylet cap and cannula hub of the second embodiment with the interlocking flanges of the stylet cap disengaged.
Figure 11:
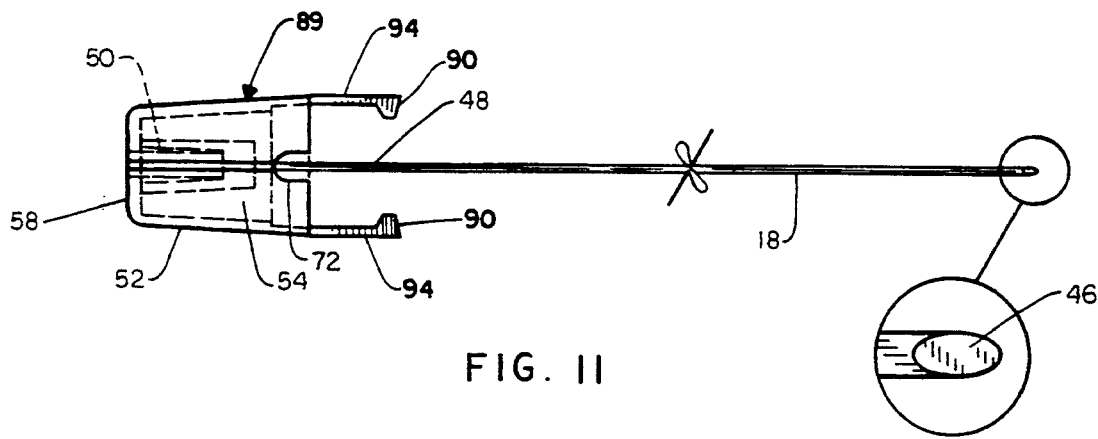
FIG. 11 is a top plan view of the third embodiment of the stylet cap and stylet.

A second embodiment of the stylet cap and cannula hub is seen in FIGS. 9 and 10. The cannula hub 71 of the second embodiment is identical to the first embodiment of the cannula hub 16 discussed above (FIGS. 1-8) except that the cannula hub of the second embodiment does not include the third projection 74. The stylet cap 73 of the second embodiment is similar to that described above in the first embodiment, except for the indicators of the alignment of the cannula 14 and stylet 18. The indicators of the second embodiment comprise a detent 84 extending from one of the cannula hub 71 or stylet cap 73 and a depression 86 provided in the other of the cannula hub 71 or stylet cap 73. In the second embodiment, a pair of detents 84 are mounted on the distal ends of a pair of flexible arms 76 which extend from the stylet cap 73. The depressions 86 are mounted on the cannula hub 71 and cooperate with the detents 84 when the stylet 18 and cannula 14 are in a predetermined angular relation. As seen in FIG. 9, the detents 84 are received within the depressions 86 when the stylet 18 is received within the lumen 22 of the cannula 14 and the distal end 24 of the cannula 14 lies along the same plane as the distal end 46 of the stylet 18.

Preferably, the flexible arms 76 of the second embodiment are integrally molded into the stylet cap 73 such that when the stylet 18 is properly and fully received within the cannula 14, each detent 84 is received within the corresponding depression 86 of the cannula hub 71. The stylet 18 is removed from the cannula 14 by squeezing a spring portion 80 of the flexible arms 76. This squeezing action causes the detents 84 mounted on the flexible arms 76 to pivot outward and be removed from the depressions 86 of the cannula hub 16. Now, the stylet 18 can be removed from the cannula 14.

The other indicators described in the first embodiment can also be incorporated into the second embodiment. For example, the visual indicator of a longitudinal rib 66 mounted on a top 54 of the cap can be incorporated. The rib 66 extends along the longitudinal axis of the stylet 18. The first projection 68 is mounted on one side of the cannula hub 16. When the stylet 18 is properly aligned with the cannula 14, the longitudinal rib 66 and the first projection 68 are both on the same side of the needle 12 and are aligned along the longitudinal axis of the needle 12, as seen in FIG. 8.

As described earlier, the user may visually observe the longitudinal rib 66 and first projection 68 to ensure proper alignment of the stylet 18 and cannula 14. Alternatively, the user may evaluate the orientation by placing his or her thumb or finger on the top of the stylet cap 54 and feel that the longitudinal rib 66 and first projection are on the same side of the needle 12.

The additional indicator comprising the previously described second projection 70 on one side of the cannula hub 71 and slot 72 of the top 54 of the stylet cap 73 are preferably incorporated into the second embodiment. The second projection 70 is selectively received within the slot 72 of the stylet cap 73 when the styler 18 is properly inserted within the cannula 14, as seen in FIG. 8.

The indicators of the second embodiment may be modified by utilizing a single flexible arm extending from one side of the stylet cap 73 and a single depression 86 mounted on one side of the cannula hub 71. The indicators may also be modified by incorporating a pair of arms 76 on the stylet cap 73 of different lengths. The detents 84 mounted at the ends of the arms of different lengths are selectively received in the depressions 86. The depressions 86 are preferably mounted on opposite sides of the cannula hub 71 and are aligned with the detents 84 such that the detents 84 are received in the depressions only when the stylet 18 and cannula 14 are in a predetermined angular relation.

Figure 12:
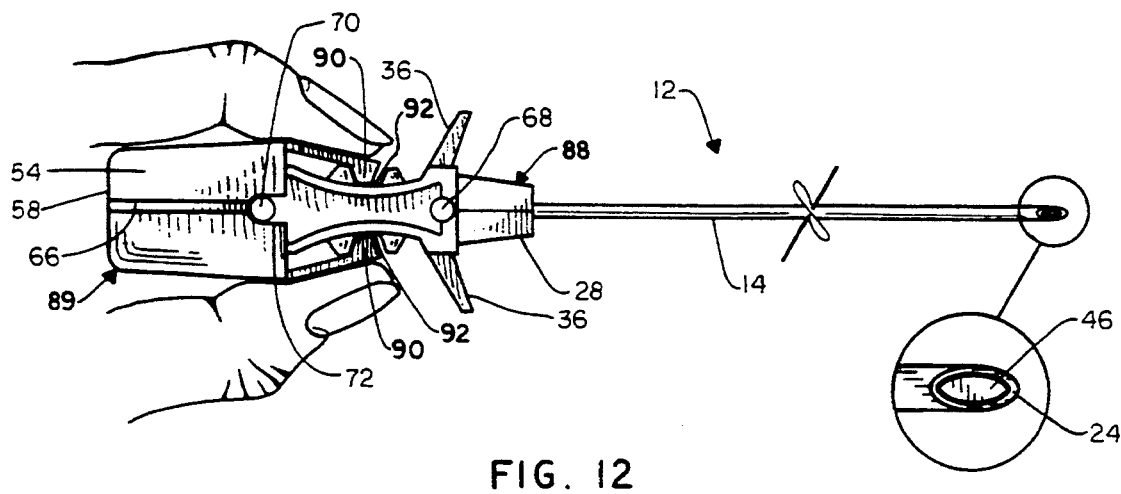
FIG. 12 is a top plan view of the third embodiment of the stylet cap and cannula hub interconnected.
Figure 13:
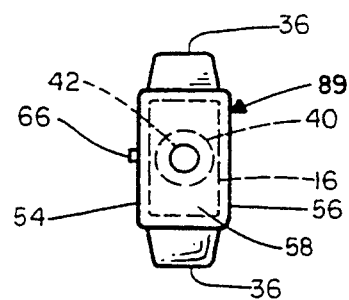
FIG. 13 is an end elevational view of the stylet cap and cannula hub of the third embodiment.
Figure 14:
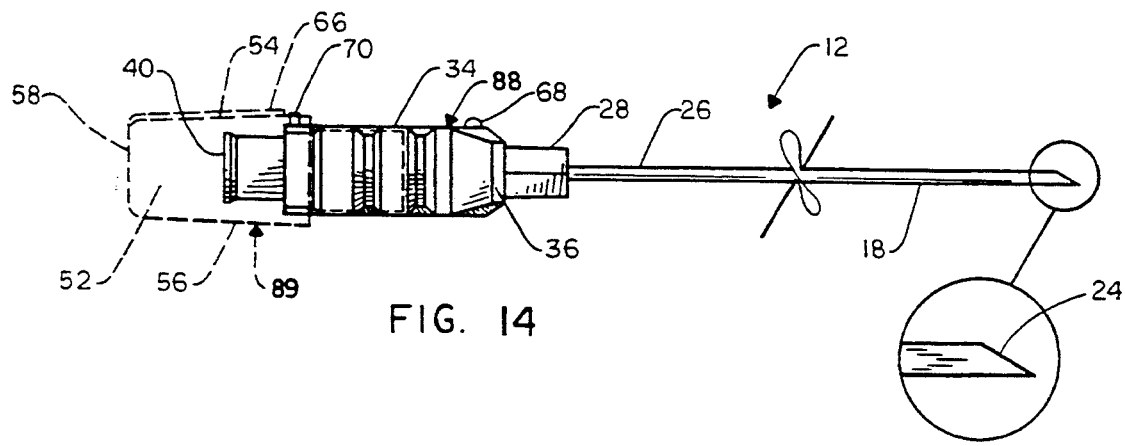
FIG. 14 is a side elevational view of the third embodiment of the stylet cap and cannula hub with the stylet cap shown in phantom lines.

The third embodiment of the needle, according to the invention, is seen in FIGS. 11-15. The cannula hub 88 of the third embodiment is identical to the second embodiment of the cannula hub 71 discussed above. The stylet cap 89 of the third embodiment is similar to that described above in the first and second embodiments, except for the indicators of the alignment of the cannula 14 and stylet 18. The indicators of the third embodiment comprise a detent 90 extending from one of the cannula hub 88 or stylet cap 89, and a depression 92 provided in the other of cannula hub 88 or stylet cap 89. In the third embodiment, a pair of detents 90 are mounted on the distal ends of a pair of arms 94 which extend from the stylet cap 89. The depressions 92 are mounted on the cannula hub 88 and cooperate with the detents 90 when the stylet 18 and the cannula 14 are in a predetermined angular relation. As seen in FIG. 12, the detents 90 are received within the depressions 92 when the stylet 18 is received within the lumen 22 of the cannula 14 and the distal end 24 of the cannula 14 and the distal end 46 of the stylet 18 are in the desired orientation.

The indicators of the third embodiment may be modified by utilizing a single depressible arm 94 extending from one side of the stylet cap 89 and a single depression 92 mounted on the one side of the cannula hub 88. The indicators may also be modified by incorporating a pair of arms 94 on the stylet cap 89 of different lengths. The detents 90 mounted at the ends of the arms 94 are selectively received in the depressions 92. The depressions 92 are preferably mounted on the opposite sides of the cannula hub 88 and are aligned with the detents 90 such that the detents 90 are received in the depressions only when the stylet 18 and cannula 14 are in a predetermined angular relation as seen in FIG. 12.

The other indicators described in the first and second embodiments can also be incorporated into the third embodiment. For example, the visual indicator of the longitudinal rib 66 and first projection 68 can be incorporated and utilized as described above. In addition, the second projection 70 and slot 72 of the cannula hub and stylet cap can be incorporated in the third embodiment and utilized as described above. Finally, the third projection 74 and recess 75 of the cannula hub and stylet cap as described in the first embodiment can be incorporated in the third embodiment.

Figure 15:
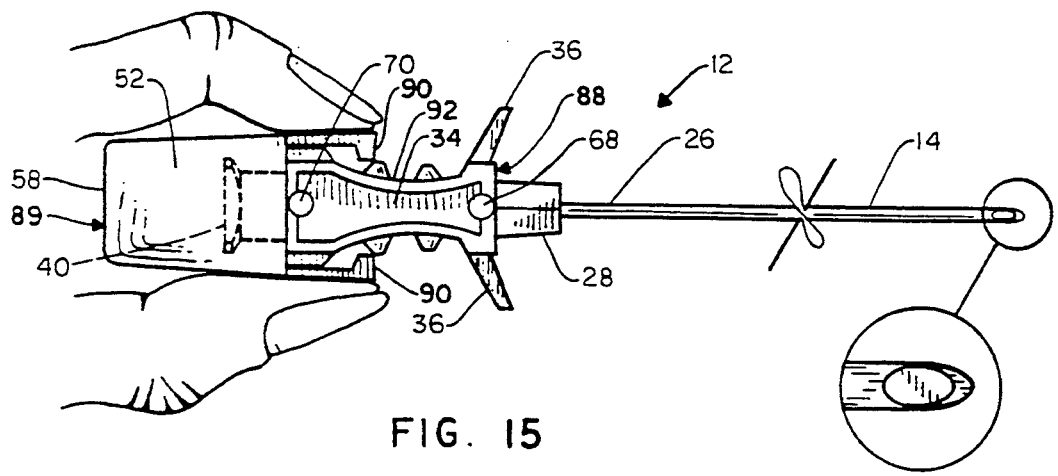
FIG. 15 is a top plan view of the third embodiment of the stylet cap mounted incorrectly on the cannula hub.

FIG. 15 shows the stylet cap 20 of the third embodiment mounted incorrectly on the cannula hub 16. As seen herein, the second projection 70 is not received within the slot 72. In addition, the detents 90 mounted at the ends of the flexible arms 94 are not received within the depressions 92 of the cannula hub 16. In addition, the longitudinal rib 66 is not aligned on the same side of the stylet as the first projection 68. With each of these several indicators, the user can quickly detect the misalignment of the stylet cap 20 with respect to the cannula hub 16.

The surgical needle 12 according to the invention provides several different indicators for ensuring the proper alignment of the stylet 18 within the cannula 14. These include mechanical interengagement of the stylet cap and cannula hub, visual coordination between the stylet cap and cannula hub, and the user's ability to feel the misalignment of the stylet cap and cannula hub with his or her finger or thumb. The incorporation of the several different indicators for determining the alignment of the stylet 18 with respect to the cannula 14 results in a safer and simpler surgical needle suitable for use in any medical procedure wherein proper alignment of the cannula and the stylet is necessary. While each of the several embodiments described above includes more than one indicator for evaluating the alignment of the stylet with respect to the cannula, it is to be understood that a stylet and cannula within the scope of the invention could incorporate only one of the indicators described or a combination thereof.

While the invention has been described in connection with specific embodiments thereof, it will be understood that this is by way of illustration and not of limitation and that the scope of the appended claims should be construed as broadly as the prior art will permit.

The embodiments of the invention in which an exclusive property or privilege is claimed are defined as follows:

1. In a surgical needle including a cannula member and a stylet member, the cannula member comprising a cannula handle and a cannula having a proximal end affixed to the cannula handle and a distal end opposite the cannula handle, the stylet member comprising a stylet handle and a stylet having a proximal end affixed to the stylet handle and a distal end opposite the stylet handle, the stylet being removably receivable within the lumen of the cannula, the axial dimensions of the stylet and the cannula being so related that when the stylet is fully received within the cannula with the handles adjacent to each other the respective distal ends are coterminous, the distal ends being respectively contoured to form a predetermined needle tip configuration when the stylet is fully received in the lumen of the cannula in predetermined angular relation therewith, the improvement wherein:

one of the handles includes a receivable projection formed on an exterior surface; and the other of the handles comprises a hollow body having a locking recess formed on an interior surface thereof, said other handle receiving at least a portion of said one handle within the hollow body when the stylet is fully received in the cannula, the receivable projection and locking recess being so formed and situated that the receivable projection is snap-locked in the locking recess when the cannula and stylet are in said predetermined angular relation.

2. A surgical needle according to claim 1 further comprising at least one guide projection mounted on one of the handles and a longitudinal rib mounted on the other of said handles wherein the at least one guide projection and longitudinal rib are aligned when the stylet and the cannula are in said predetermined angular relation.

3. A surgical needle according to claim 2 further comprising a slot in one of said handles whereby said at least one projection is received in said slot when the stylet and the cannula are in said predetermined angular relation.

4. A surgical needle according to claim 1 further comprising a reservoir in said cannula handle which is in fluid communication with said lumen of the cannula.

5. A surgical needle according to claim 4 further comprising a syringe mounting attached to one end of the cannula handle and an aperture extending through the mounting wherein said aperture is in fluid communication with said reservoir of the cannula handle.

6. A surgical needle according to claim 1 wherein said contoured distal end of the cannula is angled at an acute angle with respect to the longitudinal axis of the cannula and said contoured distal end of said stylet is angled such that it lies on the same plane as the contoured end of the cannula when the styler is fully received in the lumen of the cannula in said predetermined angular relation therewith.

7. A surgical needle according to claim 1 wherein said other handle is deformable to selectively disengage the receivable projection from the recess.

8. A surgical needle according to claim 1 wherein the one of the handles is the stylet handle and the other of the handles is the cannula handle.

9. A surgical needle according to claim 1 wherein the locking recess comprises a depression formed in the interior surface said other handle.

10. A surgical needle according to claim 1 further comprising a second receivable projection provided on one of the handles and a sliding recess mounted on the other of the handles, the sliding recess being complementary in shape to the second receivable projection and the second receivable projection being slidably received in the sliding recess when the stylet and the cannula are in said predetermined angular relation.

11. A surgical needle according to claim 10 wherein the receivable projection second depends from the stylet handle and the recess sliding is formed in the cannula handle.

12. A surgical needle according to claim 11 wherein the stylet and cannula handles are adapted such that the stylet handle must be deformed by squeezing its hollow body in order to selectively engage or disengage the receivable projection from the locking recess, thereby mounting the stylet and cannula in the predetermined angular relation or removing the stylet from the predetermined angular relation with the cannula.

* * * * *

UNITED STATES PATENT AND TRADEMARK OFFICE
CERTIFICATE OF CORRECTION

PATENT NO. : 5,336,191
DATED : August 9, 1994
INVENTOR(S) : Davis et al.

It is certified that error appears in the above-indentified patent and that said Letters Patent is hereby corrected as shown below:

```
Claim 6, column 10, line 14, "styler" should read --stylet--.
Claim 11, column 10, line 35, "the receivable projection second" should
read --the second receivable projection--.
Claim 11, column 10, line 36, "recess sliding" should read --sliding
recess--.
```

Signed and Sealed this

Thirty-first Day of October 1995

Attest:

BRUCE LEHMAN

*Attesting Officer*     *Commissioner of Patents and Trademarks*